US011647993B2

(12) United States Patent
White, Sr. et al.

(10) Patent No.: US 11,647,993 B2
(45) Date of Patent: May 16, 2023

(54) ORAL FLUID COLLECTOR

(71) Applicant: Research Triangle Institute, Research Triangle Park, NC (US)

(72) Inventors: Robert Merrifield White, Sr., Naples, FL (US); John Malcolm Mitchell, Hillsborough, NC (US); Edwin Dale Hart, Cary, NC (US)

(73) Assignee: Research Triangle Institute, Research Triangle Park (NC)

( * ) Notice: Subject to any disclaimer, the term of this patent is extended or adjusted under 35 U.S.C. 154(b) by 274 days.

(21) Appl. No.: 16/225,019

(22) Filed: Dec. 19, 2018

(65) Prior Publication Data

US 2019/0192123 A1 Jun. 27, 2019

Related U.S. Application Data

(60) Provisional application No. 62/609,901, filed on Dec. 22, 2017.

(51) Int. Cl.
*A61B 10/00* (2006.01)
*G01N 33/94* (2006.01)
*G01N 33/53* (2006.01)

(52) U.S. Cl.
CPC ...... *A61B 10/0051* (2013.01); *A61B 10/0096* (2013.01); *G01N 33/946* (2013.01); *A61B 2010/0009* (2013.01); *G01N 33/53* (2013.01)

(58) Field of Classification Search
CPC ............ A61B 10/0051; A61B 10/0096; A61B 2010/0009; G01N 33/946; G01N 33/53; A61K 9/19; A61K 9/16; F26B 5/06; A61J 19/00; A61J 19/02
See application file for complete search history.

(56) References Cited

U.S. PATENT DOCUMENTS

| | | | |
|---|---|---|---|
| 4,810,633 A * | 3/1989 | Bauer | C12Q 1/26 435/25 |
| 5,609,160 A * | 3/1997 | Bahl | A61B 10/0051 600/584 |
| 6,423,550 B1 | 7/2002 | Jenkins et al. | |
| 6,634,243 B1 | 10/2003 | Wickstead et al. | |
| 7,257,991 B2 | 8/2007 | Wickstead et al. | |
| 7,507,374 B2 | 3/2009 | Gould et al. | |
| 7,695,953 B2 | 4/2010 | Gould et al. | |
| 7,977,107 B2 | 7/2011 | Day et al. | |
| 8,025,849 B2 | 9/2011 | Baldwin et al. | |
| 8,025,851 B2 | 9/2011 | Slowey et al. | |
| 8,376,982 B2 | 2/2013 | Gould et al. | |
| 8,414,846 B2 | 4/2013 | Gold et al. | |
| 9,593,325 B2 * | 3/2017 | Bendzko | C12N 9/2462 |
| 2003/0059766 A1 * | 3/2003 | Goertz | G01N 33/5432 435/5 |
| 2003/0205097 A1 | 11/2003 | Wickstead et al. | |
| 2004/0014203 A1 | 1/2004 | Wickstead et al. | |
| 2006/0078955 A1 | 4/2006 | Lin et al. | |
| 2006/0116333 A1 * | 6/2006 | Komeda | A61P 43/00 514/27 |
| 2009/0030342 A1 * | 1/2009 | Flanigan | B01L 3/5029 600/572 |
| 2009/0306543 A1 * | 12/2009 | Slowey | A61B 10/0051 600/576 |
| 2010/0009431 A1 * | 1/2010 | Cho | B01L 3/50273 422/68.1 |
| 2010/0184082 A1 * | 7/2010 | Wang | C07K 16/16 435/7.1 |
| 2015/0173883 A1 * | 6/2015 | Ingber | A61L 29/085 435/287.2 |
| 2015/0190122 A1 * | 7/2015 | Butlin | A61B 10/0051 600/573 |

OTHER PUBLICATIONS

Musshoff et al., Cocaine and benzoylecgonine concentrations in fluorinated plasma samples of drivers under suspicion of driving under influence, Jul. 15, 2010, Forensic Science International, vol. 200, pp. 67-72 (Year: 2010).*
Politi et al., Application of Liquid Chromatography-Mass Spectrometry in Doping Control, Jan./Feb. 2005, Journal of Analytical Toxicology, vol. 29, pp. 1-14 (Year: 2005).*
Crouch, Dennis J., "Oral fluid collection: The neglected variable in oral fluid testing", Forensic Science International, 2005, pp. 165-173, vol. 150(2-3).
Kauert Gerold F., et al., "Assay of Δ9-Tetrahydrocannabinol (THC) in Oral Fluid—Evaluation of the OraSure Oral Specimen Collection Device", Journal of Analytical Toxicology, May 2006, pp. 274-277, vol. 30(4).
Langel, Kaarina, et al., "Drug Testing in Oral Fluid—Evaluation of Sample Collection Devices", Journal of Analytical Toxicology, Jul./Aug. 2008, pp. 393-401, vol. 32(6).
Quintela, Oscar, et al., "Recovery of Drugs of Abuse from the Immunalysis Quantisal Oral Fluid Collection Device", Journal of Analytical Toxicology, Oct. 2006, pp. 614-616, vol. 30(8).

(Continued)

*Primary Examiner* — Jill A Warden
*Assistant Examiner* — John McGuirk
(74) *Attorney, Agent, or Firm* — NK Patent Law

(57) ABSTRACT

An oral fluid collection device is provided that includes a borosilicate glass collection tube that can be capped post-collection for containing a human donor's expectorated oral fluid. The collection tube has a lyophilized reagent disposed therein that is essentially free of surfactants and solvents and includes a bacteriostatic, a peptidoglycan cleaving enzyme, an esterase inhibitor, an antioxidant, and a buffer at a pH range of about 5.7 to about 6.5 for stabilizing drugs and drug metabolites that may be present in the donor oral fluid. Interaction between the collected oral fluid and the buffer-preservative is provided by gravity drawing the collected oral fluid downward into contact with the lyophilized buffer-preservative. The lyophilized buffer-preservative brings the collected oral fluid to a pH for stabilization of the drugs and drug metabolites including $\Delta^9$-tetrahydrocannabinol (THC), the major metabolite of THC, 11-nor-$\Delta^9$-tetrahydrocannabinol-9-carboxylic acid, (THCA), cocaine, and the major metabolite of cocaine, benzoylecgonine (BZE).

9 Claims, No Drawings

(56) References Cited

OTHER PUBLICATIONS

Speedy, T., et al., "Development and validation of the Cozart DDS oral fluid collection device", Forensic Science International, 2007, pp. 117-120, vol. 170(2-3).

* cited by examiner

ORAL FLUID COLLECTOR

CROSS-REFERENCE TO RELATED APPLICATION

This application claims the benefit of priority of U.S. provisional patent application No. 62/609,901 titled "ORAL FLUID COLLECTOR," filed on Dec. 22, 2017, which is incorporated its entirety by this reference.

TECHNICAL FIELD

The presently disclosed subject matter relates to an oral fluid collector for drug and other small molecule testing.

BACKGROUND

Urine is the biological matrix most often employed for clinical, post-mortem, and employment-related toxicology. However, while urine can be used to identify drugs and metabolites, it has limited use in the correlation of xenobiotic levels and clinical state. In contrast, small molecules such as drugs and drug metabolites can be extracted from oral fluid in order to demonstrate their true level. Thus, a number of oral fluid testing devices are available, but they all suffer from one or both of a lack of accuracy and reproducibility.

While the levels of drugs and drug metabolites can be accurately measured from oral fluid, oral fluid as a matrix is unpredictable in a large number of instances. For example, given several different neat oral fluid samples in separate non-silanized glass tubes, one specimen might produce a solid precipitate while another might develop a string-like series of (probably) proteinaceous fibers. Other samples may remain crystal clear and colorless and almost as fluid as water for days or even weeks of sitting at ambient temperature, while a different specimen may form a gel that remains for weeks to months at room temperature. Gels, precipitates, and protein fibers may be broken up and, in some cases, actually be re-dissolved after minutes to hours of inversion or movement on a lateral-motion laboratory shaker. In other cases, a neat oral fluid gel is refractory to re-dissolution or even breaking up. In addition, neat oral fluid samples produce a precipitate of cells and other oral cavity debris regardless of whether the upper fluid layer precipitates or coagulates. Thus, the form of a neat oral fluid after standing for hours to days is unpredictable.

A number of oral fluid collection devices are currently on the market. The devices range from those in the form of a tube, such as a Falcon tube, into which a subject expectorates, or those in the form of a fibrous pad onto which a subject's oral fluid is collected and later added to a solution for analysis. The devices attempt to address the issue of the unpredictable sample instability by providing a fluid with a buffer or other preservative solution into which the oral fluid is diluted. Such dilution, which generally leads to enhanced stabilization of the oral fluid matrix, is accomplished either by direct dilution into (e.g., in the case of the devices in the form of a tube) or by placement of the device onto which oral fluid has been collected (e.g., in the case of the devices in the form of a fibrous pad) into a buffer/preservative. In regard to THC, THC in expectorated oral fluid is less stable than THC in device buffers[5] and is also not stable under fluorescent lights, with losses greater than 50% reported over 14 days; in the dark at room temperature the losses were only 20%.[6] In some cases the device includes a splitting mechanism such that the collected oral fluid is deposited into two separate tube shaped compartments rather than a single tube.

There remains an unmet need for an improved device for collection and testing of oral fluids for drugs and other small molecules that does not suffer from one or both of a lack of accuracy and reproducibility. The present disclosure provides such an improved device.

SUMMARY OF THE DISCLOSURE

In one aspect an oral fluid sample collection device is provided comprising: a borosilicate glass collection tube for receiving an oral fluid sample from a subject to be tested for one or more analytes, the collection tube having a lyophilized reagent component disposed therein, wherein the reagent component is essentially free of surfactants and solvents and comprising a bacteriostatic, a peptidoglycan cleaving enzyme, an esterase inhibitor, an antioxidant, and a buffer at a pH range of about 5.7 to about 6.5; and a cap having an inert liner to minimize adherence of the one or more analytes in the oral fluid sample and configured for engagably sealing the collection tube. The one or more analytes in the fluid sample can include one or more of drugs/drug metabolites, $\Delta^9$-tetrahydrocannabinol (THC), the major metabolite of THC (11-nor-$\Delta^9$-tetrahydrocannabinol-9-carboxylic acid (THCA), cocaine, the major metabolite of cocaine (benzoylecgonine; BZE), opiates, codeine, morphine, hydrocodone, hydromorphone, oxycodone, oxymorphone, 6-acetylmorphine, amphetamine, methamphetamine, methylenedioxymethamphetamine (MDMA), methylenedioxyamphetamine (MDA), phencyclidine (PCP), benzodiazepines, diazepam, alprazolam, ethanol, and hormones. The collection tube can be internally silanized to minimize adherence of the analyte(s) in the fluid sample.

In one aspect, a process is provided for producing an oral fluid sample collection device, comprising: depositing a liquid reagent component into an empty borosilicate glass collection tube for receiving an oral fluid sample from a subject to be tested for one or more analytes, wherein the reagent component comprises a bacteriostatic, a peptidoglycan cleaving enzyme, an esterase inhibitor, an antioxidant, and a buffer at a pH range of about 5.7 to about 6.5; and lyophilizing the reagent component within the collection tube to a point wherein the reagent component is essentially free of surfactants and solvents and has a moisture content as low as achievable by standard freeze drying technique.

In one aspect, a method is provided for collecting an oral fluid sample from a subject for analysis, comprising: a subject to be tested for one or more analytes expectorating an oral fluid sample into a borosilicate glass collection tube, the collection tube having a lyophilized reagent component disposed therein, wherein the reagent component is essentially free of surfactants and solvents and comprising a bacteriostatic, a peptidoglycan cleaving enzyme, an esterase inhibitor, an antioxidant, and a buffer at a pH range of about 5.7 to about 6.5; and engagably sealing the collection tube with a cap having an inert liner.

DETAILED DESCRIPTION OF THE DISCLOSURE

According to one aspect of the present invention, a device is provided for collection of neat or undiluted oral fluid whose volume is not substantially modified by the presence of a lyophilized buffer/preservative combination in the collection device that is buffered to a pH region where common drugs are stabilized. The oral fluid collection device of the present invention is advantageous in that it provides accuracy and reproducibility to testing for the presence of drugs and other small molecules in human oral fluid. The drugs and drug metabolites as well as hormones and other small organic biomolecules that can be tested with the collection device include, but are not limited to, $\Delta^9$-tetrahydrocannabinol (THC), the major metabolite of THC (11-nor-$\Delta^9$-tetrahydrocannabinol-9-carboxylic acid (THCA), cocaine, the major metabolite of cocaine (benzoylecgonine; BZE), opiates, codeine, morphine, hydrocodone, hydromorphone, oxycodone, oxymorphone, 6-acetylmorphine, amphetamine, methamphetamine, methylenedioxymethamphetamine (MDMA), methylenedioxyamphetamine (MDA), phencyclidine (PCP), benzodiazepines, diazepam, alprazolam, and ethanol.

More specifically, the oral fluid sample collection device of the present invention includes a borosilicate glass collection tube for receiving an oral fluid sample from a subject to be tested for one or more analytes. The collection tube has a lyophilized reagent component disposed therein that is essentially free of surfactants and solvents. The reagent component includes a bacteriostatic, a peptidoglycan cleaving enzyme, an esterase inhibitor, an antioxidant, and a buffer at a pH range of about 5.7 to about 6.5. Interaction between the collected oral fluid and the buffer-preservative is provided by gravity drawing the collected oral fluid downward into contact with the lyophilized buffer-preservative. The collection tube can be internally silanized to minimize adherence of the analyte(s) in the fluid sample to the tube. The collection tube may also include a demarcation on the tube indicating a 2 and/or 4 milliliter fluid level. The demarcation may be on the outside of the tube.

The device also includes a cap that is configured for engagably sealing the collection tube. The cap has an inert liner to minimize adherence of the one or more analytes in the oral fluid sample. Each of the collection tube and the cap can include threads for engagably sealing the collection tube by screwing the cap onto the threads of the glass collection tube.

Unless otherwise defined, all technical terms used herein have the same meaning as commonly understood by one of ordinary skill in the art to which this disclosure belongs.

Articles "a" and "an" are used herein to refer to one or to more than one (i.e. at least one) of the grammatical object of the article. By way of example, "an element" means at least one element and can include more than one element.

After collection and during storage, neat oral fluid can often form precipitates or form into a gel in the absence of stabilizing agents. The presence of the lyophilized reagent component in the collection tube of the present invention inhibits this process and also can stabilize the drugs, drug metabolites and/or hormones or other small biomolecules present in the collected oral fluid. The reagent component includes a bacteriostatic, a peptidoglycan cleaving enzyme, an esterase inhibitor, an antioxidant, and a buffer at a pH range of about 5.7 to about 6.5. For example, the presence of the peptidoglycan cleaving enzyme in the reagent component breaks down bacterial cell walls leading to breaking up of bacterial clumps in the oral fluid. The reagent component can also include one or both of a protease, such as trypsin, and an O-glycosidase, which function to cleave mucins in the oral fluid to inhibit the precipitation and/or gelation of the collected oral fluid sample. In the reagent component of the present invention, the peptidoglycan cleaving enzyme can be lysozyme. The buffer can be a phosphate buffer. The bacteriostatic can include gentamicin. The esterase inhibitor can include fluoride. The antioxidant can include a catechin. More specifically, the catechin can comprise epicatechin.

In one aspect of the present invention, a process is provided for producing an oral fluid sample collection device, comprising: depositing a liquid reagent component into an empty borosilicate glass collection tube for receiving an oral fluid sample from a subject to be tested for one or more analytes, wherein the reagent component comprises a bacteriostatic, a peptidoglycan cleaving enzyme, an esterase inhibitor, an antioxidant, and a buffer at a pH range of about 5.7 to about 6.5; and lyophilizing the reagent component within the collection tube to a point where the reagent component is essentially free of surfactants and solvents and has a moisture content as low as achievable by standard freeze drying technique. The process can further include packaging the collection tube separately or in combination with a cap having an inert liner to minimize adherence of the one or more analyte(s) in the oral fluid sample and configured for engagably sealing the collection tube.

In one aspect of the present invention, a method is provided for collecting an oral fluid sample from a subject for analysis, comprising: a subject to be tested for one or more analytes expectorating an oral fluid sample into a borosilicate glass collection tube, the collection tube having a lyophilized reagent component disposed therein, wherein the reagent component is essentially free of surfactants and solvents and comprising a bacteriostatic, a peptidoglycan cleaving enzyme, an esterase inhibitor, an antioxidant, and a buffer at a pH range of about 5.7 to about 6.5; and engagably sealing the collection tube with a cap having an inert liner.

In forensic and clinical urine toxicology, the main cannabinoid measured is 11-nor-$\Delta^9$-tetrahydrocannabinol-9-carboxylic acid (THCA or THCCOOH). THCCOOH is unstable and may be lost from both biological and synthetic matrices by a plethora of mechanisms. However, even though the stability and preservation of THCCOOH has been a challenging issue for test kit manufacturers and many forensic and clinical laboratories, the parent THC ($\Delta^9$-tetrahydrocannabinol) is even more unstable and subject to oxidative degradation, chemical rearrangement, and disappearance from various matrices due to purely physical phenomena such as surface adsorption and absorption.

In experimental studies, parent THC in neat human oral fluid modified with the reagent component described above was found to be stable over a 2-week period. Conversely, when parent THC was spiked into unmodified neat oral fluid of two donors in a drug study, substantial loss of THC was observed. By itself, parent THC appears to be most stable around pH 7.5.

It has been suggested that THCCOOH, the main metabolite of THC, may be indicative of cannabis use as opposed to possible passive exposure. If its analysis becomes routine in forensic or clinical laboratories, it should be noted that the need for deconjugation of the glucuronide conjugate, which is about two-thirds of the total THCCOOH, may need to be considered.[7]

Parent cocaine (pharmacologically active) and its major metabolite, benzoylecgonine (BZE, (pharmacologically inactive), are both of interest in oral fluid drug testing. Both have a basic nitrogen in the carbon bridge. Other metabolites such as ecgonine methyl ester, norcocaine, ecgonine itself, and minor oxidation products of cocaine and BZE may be of interest in some special studies.

Parent cocaine is a double ester while BZE has only a single ester moiety. In addition to an ester group, BZE also has a carboxylic acid function and still retains the basic bridge nitrogen, making it zwitterionic. Cocaine has very little solubility in water (1 gram dissolves in 600 mL at room temperature[8]) while BZE has considerable water solubility (the tetrahydrate can be crystallized from water in which it is soluble when the water is hot). Thus, parent cocaine can be extracted easily from aqueous matrices, especially when the analyst makes the matrix mildly basic. Conversely, BZE can be more difficult to extract from biological matrices by liquid-liquid technology and requires moderately polar solvents such as methylene chloride and chloroform. Cocaine readily decomposes to BZE even at neutral pH, and more rapidly in strong base and strong acid, as is typical of most organic esters.[9] In aqueous solution, parent cocaine appears to demonstrate its greatest stability around pH 5. In the presence of ethyl alcohol (ethanol), cocaine may transesterify to the pharmacologically active substance cocaethylene.

Based on the above discussion, the stabilization of parent cocaine in a matrix such as oral fluid, which contains esterases possibly derived from crevicular fluid, is challenging unless appropriate buffering at a pH where parent cocaine is stable is employed. Surprisingly, BZE appears stable in most matrices at a broad range of pH values.

Providing the combination of parent THC and parent cocaine in the same synthetic or human oral fluid can usually be accomplished with a compromise pH of approximately 6.5. The pH of a spiking or stock solution is also a consideration. The addition of drugs such as amphetamines or opiates (vide infra) to an unbuffered spiking solution can cause an unanticipated rise in pH, resulting in the hydrolysis of parent cocaine and 6-acetylmorphine.

Ventura et al. reported on the stability of drugs in transit for the purpose of assessing external proficiency schemes in laboratories. They evaluated two different collection devices and noted that 26% to 41% of the cocaine degrades to BZE within 48 to 72 hours respectively.[10]

In general, the stereoisomers of amphetamine, methamphetamine, methylenedioxymethamphetamine (MDMA, "ecstasy"), and methylenedioxyamphetamine (MDA), are common in oral fluid toxicology. The literature is replete with many other amphetamine derivatives that possess stimulatory and/or hallucinogenic capability and may be detected and, if necessary, quantitated in human oral fluid.

The fundamental amphetamines, amphetamine itself and methamphetamine, are basic (amphetamine[11] and methamphetamine[12] $pK_a=9.9$). Both exist in two stereoisomeric forms. The d and l forms of amphetamine and the d form of methamphetamine have stimulatory activity. The l form of methamphetamine is active only as an antihistamine.[13] Chiral analysis of methamphetamine in oral fluid can assist in distinguishing licit use (Vicks inhaler, l-form) from illicit use (d-form); for amphetamine a 3:1 ratio of d:l amphetamine may indicate Adderall ingestion.

As stated above, it can be important to consider the pH of a spiking solution or finished oral fluid control or calibrator when amphetamines are added and parent cocaine and/or 6-acetylmorphine is present. A seemingly innocuous elevation of the pH of a spiking solution or a finished synthetic or human oral fluid product can be disastrous for identifying cocaine and 6-acetylmorphine. Overcompensation for a pH elevation by reducing pH to less than 4 can result in an unexpected significant reduction of $\Delta^9$-THC due to isomerization to $\Delta^8$-THC if $\Delta^9$-THC is in the same spiking mixture.[14]

Although very few stability issues have arisen with the methylenedioxy drugs, it is worth noting that the methylenedioxy ring is the ether form of a geminal diol. Geminal diols[15] are noted for their instability, which in the case of the methylenedioxy compounds is greatly stabilized by being present as a diether but may be a potential area for unwanted chemical reactions.

Hydrochloride salts may contribute unwanted acidity and lowering of the pH of a spiking solution. Conversely, use of the free base may result in an undesirable raising of the pH of a spiking solution.

Although many chemical modifications can be made to the fundamental opiates codeine and morphine, in general they are resistant to chemical changes caused by mild oxidation and reduction during routine extraction and, where appropriate, derivatization. Despite morphine's polarity and mildly amphoteric nature, both codeine and morphine can be extracted routinely from oral fluid and analyzed.

In urine, to obtain total codeine and total morphine concentrations, deconjugation is required. The same requirement applies to blood and its products unless only free active drug concentration is desired.

Like the analysis of codeine and morphine, analysis of the semisynthetic opiates hydrocodone, hydromorphone, oxycodone, and oxymorphone is relatively unrestricted. In contrast to urinalysis for oxycodone use, the parent drug itself is predominantly identified in oral fluid, and the main metabolite is noroxycodone and not oxymorphone; likewise, norcodeine is present after codeine intake (not morphine) and norhydrocodone (not hydromorphone) after hydrocodone intake. A comprehensive review of the metabolism of prescription opioids, including codeine, hydrocodone, oxycodone, fentanyl, meperidine, methadone, buprenorphine, and tramadol was published in 2015.[16] The authors noted that oral fluid:blood ratios exceed 1 for most of these opioids, making oral fluid an excellent alternative matrix for testing of this drug class.

Two opiates which require special pre-analytical and analytical attention are heroin (diacetylmorphine) and 6-monoacetylmorphine (6-AM), which is the intermediate metabolite of diacetylmorphine. Both are labile esters. However, both molecules are stabilized at about pH 5.0. Experiments show that common collection pH of 6.5 is adequate to stabilize 6-AM. In a transit study, Ventura et al. noted that 9% to 12% of 6-AM converted to morphine within 48 hours.[10]

Pain management and prescription medication compliance are areas where the utility of oral fluid testing is gaining wide acceptance. Several publications indicate similar or better detection rates for drugs in oral fluid compared to urine.[17,18] The interpretation of oral fluid opioid concentrations for therapeutic and forensic purposes is also gaining traction and will be an area of future research.[19,20]

As a class of compounds, the 1,4-benzodiazepines are pharmacodynamically potent but chemically unstable. They demonstrate pH, light, and oxidation sensitivity. Perhaps, the only two stable ones for immunoassay calibration and control are nitrazepam (not approved for use in the United States) and nordiazepam (metabolite of diazepam).

The amino-metabolites of flunitrazepam, nitrazepam, and clonazepam are present at higher concentration and are more stable than the parent drugs in oral fluid.[21] From 1001 samples positive for clonazepam and its main metabolite 7-aminoclonazepam, both were detected in 70.6%, only clonazepam in 6.3%, and only the metabolite in 23% of the specimens. For nitrazepam the numbers were similar: both drug and metabolite were present in 65.8% of specimens, the parent drug only in 7.5%, and metabolite only in 26.5%.[22]

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

REFERENCES

1. Lehman A P, "Perspectives on Risk Assessment," SOT FDA Colloquia on Emerging Toxicological Science. Challenges in Food and Ingredient Safety, Jun. 17, 2015.

2. White R M, Instability and poor recovery of cannabinoids in urine, oral fluid, and hair, to be published, Forensic Sci Rev, January 2018.

3. White R M, Hart E D, Mitchell J M, SAMHSA Oral Fluid Pilot PT, 2011-2017.

4. White R M, Sutheimer C, Mitchell J M, Hart E D, Weber F X, Lodico C, The influence of zinc-containing over-the-counter products and an oral rinse on oral fluid drug testing, Submitted for publication.

5. Lee D, Milman G, Schwope D M, Barnes A J, Gorelick D A, Huestis M A. Cannabinoid stability in authentic oral fluid after controlled cannabis smoking. *Clin Chem.* 2012; 58(7):1101-1109.

6. Moore C, Vincent M, Rana S, Coulter C, Agrawal A, Soares J. Stability of □9-tetrahydrocannabinol (THC) in oral fluid using the Quantisal collection device. *Forens Sci Int.* 2006; 164:126-130.

7. Moore C, Rana S, Coulter C, Day D, Vincent M, Soares J. Detection of conjugated 11-nor-□⁹-tetrahydrocannabinol-9-carboxylic acid in oral fluid. *J Anal Toxicol.* 2007; 31(4): 187-194.

8. The Merck Index, Fifteenth Edition, The Royal Society of Chemistry, Thomas Graham House, Cambridge, 2013.

9. Chapter 18, "Organic Chemistry, Sixth Edition," Brown W H, Foote C S, Iverson B L, Anslyn E V, Novak B M, Brooks/Cole, Belmont, Calif., 2012.

10. Ventura M, Pichini S, Ventura R, Leal S, Zuccaro P, Pacifici R, de la Torre R. Stability of drugs of abuse in oral fluid collection devices with purpose of external quality assessment schemes. *Ther Drug Monit.* 2009; 31(2):277-280. doi:10.1097/FTD.0b013e318198670b 11. Amphetamine, p. 122, Disposition of Toxic Drugs and Chemicals in Man, Tenth Edition, R C Baselt, Editor, Biomedical Publications, Seal Beach, Calif., 2014.

12. d-Methamphetamine, p. 1263, Disposition of Toxic Drugs and Chemicals in Man, Tenth Edition, R C Baselt, Editor, Biomedical Publications, Seal Beach, Calif., 2014.

13. 1-Methamphetamine, p. 1266, Disposition of Toxic Drugs and Chemicals in Man, Tenth Edition, R C Baselt, Editor, Biomedical Publications, Seal Beach, Calif., 2014.

14. Garrett E R, Tsau J, Stability of the tetrahydrocannabinols I, *J Pharm Sci* 63:1563; 1974.

15. Chapter 16, "Organic Chemistry, Sixth Edition," Brown W H, Foote C S, Iverson B L, Anslyn E V, Novak B M, Brooks/Cole, Belmont, Calif., 2012.

16. DePriest A Z, Puet B L, Holt A C, Roberts A, Cone E J. Metabolism and disposition of prescription opioids: A Review. *Forensic Sci Rev.* 2015; 27(2):115-145.

17. Kunkel F, Fey E, Borg D, Stripp R, Getto C. Assessment of the use of oral fluid as a matrix for drug monitoring in patients undergoing treatment for opioid addiction. *J Opioid Manag.* 2015; 11(5):435-442. doi: 10.5055/jom.2015.0293.

18. Conermann T, Gosalia A R l, Kabazie A J, Moore C, Miller K, Fetsch M, Irvan D. Utility of oral fluid in compliance monitoring of opioid medications. *Pain Phys.* 2014; 17(1):63-70.

19. Moore C, Kelley-Baker T, Lacey J Interpretation of oxycodone concentrations in oral fluid. *J Opioid Manag.* 2012; 8(3):161-166. doi: 10.5055/jom.2012.0112.

20. Shaparin N, Mehta N, Kunkel F, Stripp R, Borg D, Kolb E. A novel chronic opioid monitoring tool to assess prescription drug steady state levels in oral fluid. Pain Med. 2017 Feb. 23. doi: 10.1093/pm/pnw335. [Epub ahead of print]

21. Melanson S E, Griggs D, Bixho I, Khaliq T, Flood J G. 7-aminoclonazepam is superior to clonazepam for detection of clonazepam use in oral fluid by LC-MS/MS. Clin Chim Acta. 2016; 455:128-133. doi: 10.1016/j.cca.2016.01.027. Epub 2016 Jan. 27.

22. Vindenes V, Strand D H, Koksaeter P, Gjerde H. Detection of nitrobenzodiazepines and their 7-amino metabolites in oral fluid. *J Anal Toxicol.* 2016; 40(4):310-312. doi: 10.1093/jat/bkw020. Epub 2016 Mar. 23.

The invention claimed is:

1. An oral fluid sample collection device comprising:
   a borosilicate glass collection tube, the collection tube having a reagent component disposed directly therein and subsequently lyophilized within the collection tube, wherein the reagent component comprises gentamicin, lysozyme, fluoride, epicatechin, O-glycosidase, trypsin and a phosphate buffer, wherein the phosphate buffer is present in an amount sufficient for buffering the reagent component to a pH range of about 5.7 to about 6.5; and
   a cap having an inert liner, wherein the cap is configured for engageably sealing the collection tube,
   wherein, in use, a volume of oral fluid is received by the collection tube and interaction is provided between the received oral fluid and the reagent component by gravity drawing the received oral fluid downward into the collection tube and into contact with the reagent component.

2. The sample collection device of claim 1, wherein each of the collection tube and the cap comprise threads for engageably sealing the collection tube by screwing the cap onto the threads of the glass collection tube.

3. The sample collection device of claim 1, configured for receiving an oral fluid sample to be tested for one or more analytes, wherein the collection tube is internally silanized to minimize adherence of the analyte(s) in the oral fluid sample.

4. The sample collection device of claim 1, configured for receiving an oral fluid sample to be tested for one or more analytes, wherein the one or more analyte(s) comprises one or more drugs/drug metabolites selected from the group consisting of parent Δ9-tetrahydrocannabinol (THC), the major metabolite of THC, 11-nor-Δ9-tetrahydrocannabinol-9-carboxylic acid (THCA), cocaine, the major metabolite of cocaine, benzoylecgonine (BZE), opiates, codeine, morphine, hydrocodone, hydromorphone, oxycodone, oxymorphone, 6-acetylmorphine, amphetamine, methamphetamine, methylenedioxymethamphetamine (MDMA), methylenedioxyamphetamine (MDA), phencyclidine (PCP), benzodiazepines, diazepam, alprazolam, ethanol, and hormones.

5. The oral fluid sample collection device of claim 1, wherein the sample collection device does not comprise a porous pad onto which the lyophilized reagent component is disposed.

6. A process for producing an oral fluid sample collection device configured to stabilize a collected oral fluid sample after collection, comprising:
providing an empty borosilicate glass collection tube for receiving an oral fluid sample from a subject to be tested for one or more analytes,
providing for stabilization of the oral fluid sample in the collection tube prior to its collection by depositing a liquid reagent component into the empty borosilicate glass collection tube prior to collection of the oral fluid sample, wherein the reagent component comprises gentamicin, lysozyme, fluoride, epicatechin, O-glycosidase, trypsin and a phosphate buffer, wherein the phosphate buffer is present in an amount sufficient for buffering the reagent component to a pH range of about 5.7 to about 6.5; and
lyophilizing the deposited reagent component within the collection tube,
wherein, in use, a volume of oral fluid is received by the collection tube and interaction is provided between the received oral fluid and the reagent component by gravity drawing the received oral fluid downward into the collection tube and into contact with the stabilizing reagent component.

7. The process of claim 6, further comprising packaging the collection tube separately or in combination with a cap having an inert liner to minimize adherence of the one or more analyte(s) in the oral fluid sample and configured for engagably sealing the collection tube.

8. The process of claim 6, wherein the borosilicate glass collection tube is internally silanized to minimize adherence of the analyte(s) in the fluid sample.

9. A method for collecting an oral fluid sample from a subject for analysis, comprising:
providing an oral fluid collection device comprising a borosilicate glass collection tube,
providing for stabilization of the oral fluid sample in the collection tube prior to its collection by depositing a reagent component directly into the collection tube and subsequently lyophilizing the reagent component within the collection tube, wherein the reagent component provides a stabilizing function for the oral fluid sample and comprises gentamicin, lysozyme, fluoride, epicatechin, O-glycosidase, trypsin and a phosphate buffer in lyophilized form, in an amount sufficient to buffer the reagent component to a pH range of about 5.7 to about 6.5, collecting a volume of oral fluid expectorated by a subject into the collection tube; and
engageably sealing the collection tube of the oral fluid collection device with a cap having an inert liner,
wherein interaction is provided between the oral fluid and the reagent component by gravity drawing the oral fluid downward into the collection tube and into contact with the reagent component.

\* \* \* \* \*